United States Patent
Waechter-Stehle et al.

(10) Patent No.: US 9,317,919 B2
(45) Date of Patent: Apr. 19, 2016

(54) IDENTIFYING INDIVIDUAL SUB-REGIONS OF THE CARDIOVASCULAR SYSTEM FOR CALCIUM SCORING

(75) Inventors: Irina Waechter-Stehle, Hamburg (DE); Reinhard Kneser, Aachen (DE); Juergen Weese, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 281 days.

(21) Appl. No.: 13/884,617

(22) PCT Filed: Nov. 9, 2011

(86) PCT No.: PCT/IB2011/054988
§ 371 (c)(1),
(2), (4) Date: May 10, 2013

(87) PCT Pub. No.: WO2012/063204
PCT Pub. Date: May 18, 2012

(65) Prior Publication Data
US 2013/0230225 A1   Sep. 5, 2013

Related U.S. Application Data

(60) Provisional application No. 61/412,921, filed on Nov. 12, 2010.

(51) Int. Cl.
*G06K 9/00* (2006.01)
*A61B 5/04* (2006.01)
(Continued)

(52) U.S. Cl.
CPC .............. *G06T 7/0014* (2013.01); *A61B 6/463* (2013.01); *A61B 6/466* (2013.01); *A61B 6/5217* (2013.01);
(Continued)

(58) Field of Classification Search
None
See application file for complete search history.

(56) References Cited

U.S. PATENT DOCUMENTS 5,435,310 A * 7/1995 Sheehan ................ B82Y 15/00
382/128
5,601,084 A * 2/1997 Sheehan ................ B82Y 15/00
600/416
(Continued)

FOREIGN PATENT DOCUMENTS

WO   2007058997 A2   5/2007
WO   2010071896 A2   6/2010

OTHER PUBLICATIONS

Rumberger et al. "Electron Beam Computed Tomographic Coronary Calcium Score Cutpoints and Severity of Associated Angiographic Lumen Stenosis" JACC Vo. 29, No. 7, Jun. 1997 (pp. 1542-1548).*
(Continued)

*Primary Examiner* — Chan Park
*Assistant Examiner* — Mia M Thomas

(57) ABSTRACT

A method includes identifying a plurality of different anatomical sub-regions of the cardiovascular system of a subject in image data of the subject based on a subject specific cardiovascular anatomical model, wherein the plurality of different regions corresponds to regions where calcifications occur, searching for and identifying calcifications in the sub-regions based on voxel grey value intensity values of the image data, and generating a signal indicative of one or more regions of voxels of the image data respectively corresponding to sub-regions including identified calcifications. A computing system (118) includes a processor that automatically determines a plurality of different groups of voxels of image data of a subject, wherein each group of voxels corresponds to a different sub-region of the cardiovascular system of the subject and each group of voxels corresponds to a region that includes a calcification identified in the image data.

22 Claims, 3 Drawing Sheets

(51) Int. Cl.
 G06T 7/00 (2006.01)
 A61B 6/00 (2006.01)
 A61B 6/03 (2006.01)
(52) U.S. Cl.
 CPC ............ *G06T 7/0012* (2013.01); *G06T 7/0081*
 (2013.01); *A61B 6/032* (2013.01); *A61B 6/503*
 (2013.01); *A61B 6/504* (2013.01); *G06K*
 *2209/05* (2013.01); *G06T 2207/10081*
 (2013.01); *G06T 2207/20148* (2013.01); *G06T*
 *2207/30048* (2013.01); *G06T 2207/30101*
 (2013.01)

(56) References Cited

U.S. PATENT DOCUMENTS

| | | | | |
|---|---|---|---|---|
| 7,873,194 | B2* | 1/2011 | Begelman | A61B 5/02007 345/418 |
| 7,957,574 | B2* | 6/2011 | Sirohey | G06T 7/0012 382/131 |
| 8,077,939 | B2* | 12/2011 | Le Nezet | A61B 5/02007 382/128 |
| 8,885,905 | B2* | 11/2014 | Dey | A61B 6/032 382/131 |
| 8,970,578 | B2* | 3/2015 | Voros | A61B 5/02007 345/419 |
| 2003/0095695 | A1* | 5/2003 | Arnold | 382/131 |
| 2003/0176780 | A1* | 9/2003 | Arnold et al. | 600/407 |
| 2004/0133100 | A1* | 7/2004 | Naghavi | A61B 5/02007 600/425 |
| 2005/0008205 | A1* | 1/2005 | Kiraly et al. | 382/128 |
| 2005/0074158 | A1* | 4/2005 | Kaufhold | G06T 7/204 382/132 |
| 2005/0096528 | A1* | 5/2005 | Fritz | A61B 5/02007 600/407 |
| 2005/0157917 | A1* | 7/2005 | Saptharishi | A61B 6/505 382/131 |
| 2006/0111622 | A1* | 5/2006 | Merritt | A61B 5/0059 600/315 |
| 2008/0010304 | A1* | 1/2008 | Vempala | G06F 17/3071 |
| 2008/0015466 | A1* | 1/2008 | Lerman | A61B 10/06 600/567 |
| 2008/0082002 | A1* | 4/2008 | Wilson | A61B 5/02007 600/483 |
| 2008/0159610 | A1 | 7/2008 | Haas et al. | |
| 2008/0273652 | A1* | 11/2008 | Arnold et al. | 378/4 |
| 2008/0279435 | A1* | 11/2008 | Arnold et al. | 382/131 |
| 2009/0310825 | A1* | 12/2009 | Bontus et al. | 382/107 |
| 2009/0318986 | A1* | 12/2009 | Alo | A61N 1/36114 607/4 |
| 2010/0156898 | A1* | 6/2010 | Voros et al. | 345/419 |
| 2010/0215225 | A1* | 8/2010 | Kadomura | G06T 7/0012 382/128 |
| 2010/0278405 | A1* | 11/2010 | Kakadiaris | G06F 19/3431 382/131 |
| 2010/0280366 | A1* | 11/2010 | Arne | A61B 5/046 600/425 |
| 2011/0206247 | A1* | 8/2011 | Dachille | G06T 11/001 382/128 |
| 2012/0065494 | A1* | 3/2012 | Gertner | A61B 5/055 600/411 |
| 2012/0243764 | A1* | 9/2012 | Dey | A61B 6/032 382/131 |
| 2015/0199478 | A1* | 7/2015 | Bhatia | A61B 6/488 382/128 |

OTHER PUBLICATIONS

Messika-Zeitoun et al. "Evaluation and Clinical Implications of Aortic Valve Calcification Measured by Electron-Beam Computed Tomography" Circulation Online via American Heart Association, Jan. 2004 (pp. 356-362).*
Arad et al. "Coronary Calcification, Coronary Disease Risk Factors, C-Reactive Protein, and Atherosclerotic Cardiovascular Disease Events The St. Francis Heart Study" Journal of the American College of Cardiology Vo. 46, No. 1, Jul. 2005 (pp. 158-165).*
Waxman et al. "Detection and Treatment of Vulnerable Plaques and Vulnerable Patients Novel Approaches to Prevention of Coronary Events" (Circulation. 2006;114:2390-2411.) © 2006 American Heart Association, Inc pp. 1-23.*
Brunner, et al., A Heart-Centered Coordinate System for the Detection of Coronary Artery Zone in Non-Contrast Computed Tomography Data, publication date unknown, downloaded from internet 2010, 8 sheets.
Brown, et al., Coronary Calcium Coverage Score:Determination, Correlates, and Predictive Accuracy in the Multi-Ethnic Study of Atherosclerosis, Radiology, Jun. 2008, pp. 669-678, vol. 247, No. 3.
Ecabert, et al., Automatic Model-Based Segmentation of the Heart in CT Images, IEEE Transactions on Medical Imaging, Sep. 2008, pp. 1189-1201, vol. 27, No. 9.
Isgum, et al., Automated aortic calcium scoring on low-dose chest computed tomography, Med. Phys., Feb. 2010, pp. 714-723, vol. 37, No. 2.
Dey, D., et al.; Automated 3-dimensional quantification of noncalcified and calcified coronary plaqu from coronary CT angiography; 2009; Journal of Cardiovascular Computed Tomography; vol. 3:372-382.
Weese, J., et al.; Patient-specific heart models for diagnosis and interventions; 2009; Medicamundi; 53(3)72-78.

* cited by examiner

IDENTIFYING INDIVIDUAL SUB-REGIONS OF THE CARDIOVASCULAR SYSTEM FOR CALCIUM SCORING

CROSS REFERENCE TO RELATED APPLICATIONS

This application is a national filing of PCT application Serial No. PCT/IB2011/054988, filed Nov. 9, 2011, published as WO 2012/063204 A1 on May 18, 2012, which claims the benefit of U.S. provisional application Ser. No. 61/412,921 filed Nov. 12, 2010, which is incorporated herein by reference.

FIELD OF THE INVENTION

The following generally relates to imaging and more particularly to identifying individual sub-regions of the cardiovascular system for calcium scoring and is described with particular application to computed tomography (CT); however, the following is also amenable to other imaging modalities.

BACKGROUND OF THE INVENTION

A computed tomography (CT) scanner includes an x-ray tube that emits radiation that traverses an examination region and a portion of an object or subject therein. A detector detects radiation traversing the examination region and generates projection data indicative of the detected radiation. A reconstructor reconstructs the projection data and generates volumetric image data indicative of the portion of the object or subject in the examination region.

A cardiac CT scan for coronary calcium is a non-invasive way of obtaining information about the presence, location and extent of calcified plaque in the coronary arteries. Generally, calcified plaque is build-up of fat and/or other substances under the inner layer of the artery and may indicate a presence of atherosclerosis, or coronary artery disease, which indicates a risk of heart attack. Since calcium is a marker of coronary artery disease, the amount of calcium in CT data has been quantified as a calcium score through a procedure generally referred to as calcium scoring.

Conventionally, two main calcium scoring approaches exist. The first is automatic calcium scoring, which is done globally, so there is one global calcium score. The other is manual calcium scoring in which a user employs a software application to manually distinguish different regions of the coronary arteries and calcium scores are determined for the different regions. Unfortunately, such methods do not always provide the granularity of interest for all patients.

For example, for minimally invasive aortic valve implantation, the spatial distribution of calcified plaque around the aortic valve, aortic bulbus, leftventricular outflow tract and aorta is important for risk assessment and planning of the procedure. Calcium in the aorta determines the access method; the amount of calcium on the valve has an influence on the selection of the right diameter of the stent; distribution of calcium on the three (3) leaflets can have an influence on stent stability; calcium on the leftventricular outflow tract has an influence on the stability of the implanted stent.

In view of the above, there is an unresolved need for novel and non-obvious calcium scoring approaches.

SUMMARY OF THE INVENTION

Aspects of the present application address the above-referenced matters and others.

According to one aspect, a method includes identifying a plurality of different anatomical sub-regions of the cardiovascular system of a subject in image data of the subject based on a subject specific cardiovascular anatomical model, wherein the plurality of different regions corresponds to regions where calcifications occur, searching for and identifying calcifications in the sub-regions based on voxel grey value intensity values of the image data, and generating a signal indicative of one or more regions of voxels of the image data respectively corresponding to sub-regions including identified calcifications.

According to another aspect, a computing system includes a processor that automatically determines a plurality of different groups of voxels of image data of a subject, wherein each group of voxels corresponds to a different sub-region of the cardiovascular system of the subject and each group of voxels corresponds to a region that includes a calcification identified in the image data.

According to another aspect, a method includes automatically determining and visualizing calcium score for different individual sub-regions of the cardiovascular system of a subject.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
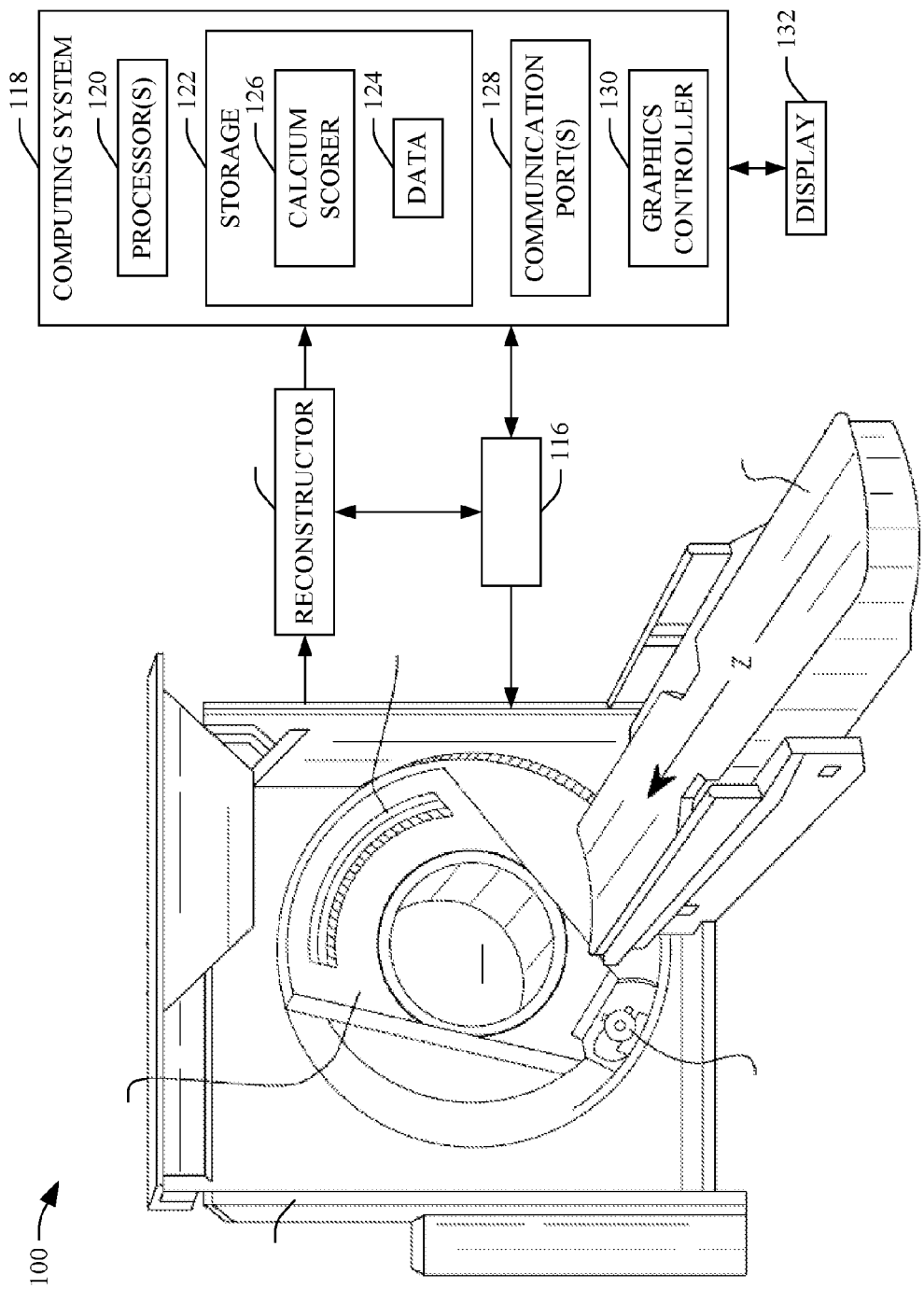
FIG. 1 illustrates an imaging system in connection with a calcium scorer.

FIG. 1 illustrates an imaging system such as a computed tomography (CT) scanner 100.

The scanner 100 includes a stationary gantry 102 and a rotating gantry 104, which is rotatably supported by the stationary gantry 102. The rotating gantry 104 rotates around an examination region 106 about a longitudinal or z-axis. A patient support 108, such as a couch, supports a patient in the examination region 106 and is movable along the z-axis in coordination with the rotation of the rotating gantry 104 to facilitate helical, axial, or other desired scanning trajectories.

A radiation source 110, such as an x-ray tube, is supported by and rotates with the rotating gantry 104 around the examination region 106. The radiation source 110 emits radiation that is collimated by a source collimator to produce a generally fan, wedge, or cone shaped radiation beam that traverses the examination region 106. A radiation sensitive detector array 112 detects radiation that traverses the examination region 106 and generates projection data indicative of the detected radiation.

A reconstructor 114 reconstructs the projection data and generates volumetric image data indicative of the examination region 106. A general purpose computing system serves as an operator console 116, and includes an output device such as a display and an input device such as a keyboard, mouse, and/or the like. Software resident on the console 116 allows the operator to control the operation of the system 100, for example, allowing the operator to initiate scanning, etc.

A computing system 118 such as a workstation, a computer, or the like is configured to process the image data. The computing system 118 includes one or more processors 120 and computer readable storage medium 122 (e.g., physical memory) encoded or embedded with computer readable instructions (e.g., software programs), which, when executed by the one or more processors 120 cause the computing system 118 to carry out various functions. The storage medium 122 also stores data 124.

Such instructions include instructions for implementing a calcium scorer 126 for calcium scoring. As described in greater detail below, the calcium scorer 126 is configured to automatically and/or semi-automatically take into account the spatial distribution of the cardiac region for calcium scoring. By way of example, for calcium scoring for coronary artery disease, the calcium scorer 126 can determine a calcium score for each part of interest of the cardiovascular system.

The calcium scores for a sub-set or all parts of the cardiac region of interest and/or combined scores can be variously presented via a graphical user interface (GUI), for example, in a table where each result is connected to a corresponding anatomical model. Additionally or alternatively, the connection can be visualized by coloring or other indicia, and/or the user can select a part of the anatomical model via a user interactive GUI where the corresponding calcium score are displayed. Additionally or alternatively, calcium scores can be mapped on a surface of the anatomical model.

One or more communication ports 128 are configured for communication with one or more input devices (e.g., a keyboard, a mouse, and the like), one or more output devices (e.g., a display, a printer, etc.), one or more apparatuses (e.g., a computing system, portable storage, etc.), one or more data repositories, the system 100 (e.g., the console 116 and/or the reconstructor 114), etc. A graphics controller 130 processes data for presentation on a monitor, such as a display 132, in a human readable format.

Although the storage medium 122 is shown as a single component, it is to be understood that the storage medium 122 may include a plurality of storage units, including storage local to the computing system 118 and/or storage external from the computing system 118. Likewise, the processors 120 may be distributed across different computing systems. Furthermore, the computing system 118 may be part of the console 116, or vice versa, or located remote from the system 100. Moreover, the one or more processors 120 may additionally or alternatively execute instructions carried by transitory medium such as a signal or wave carrier.

Figure 2:
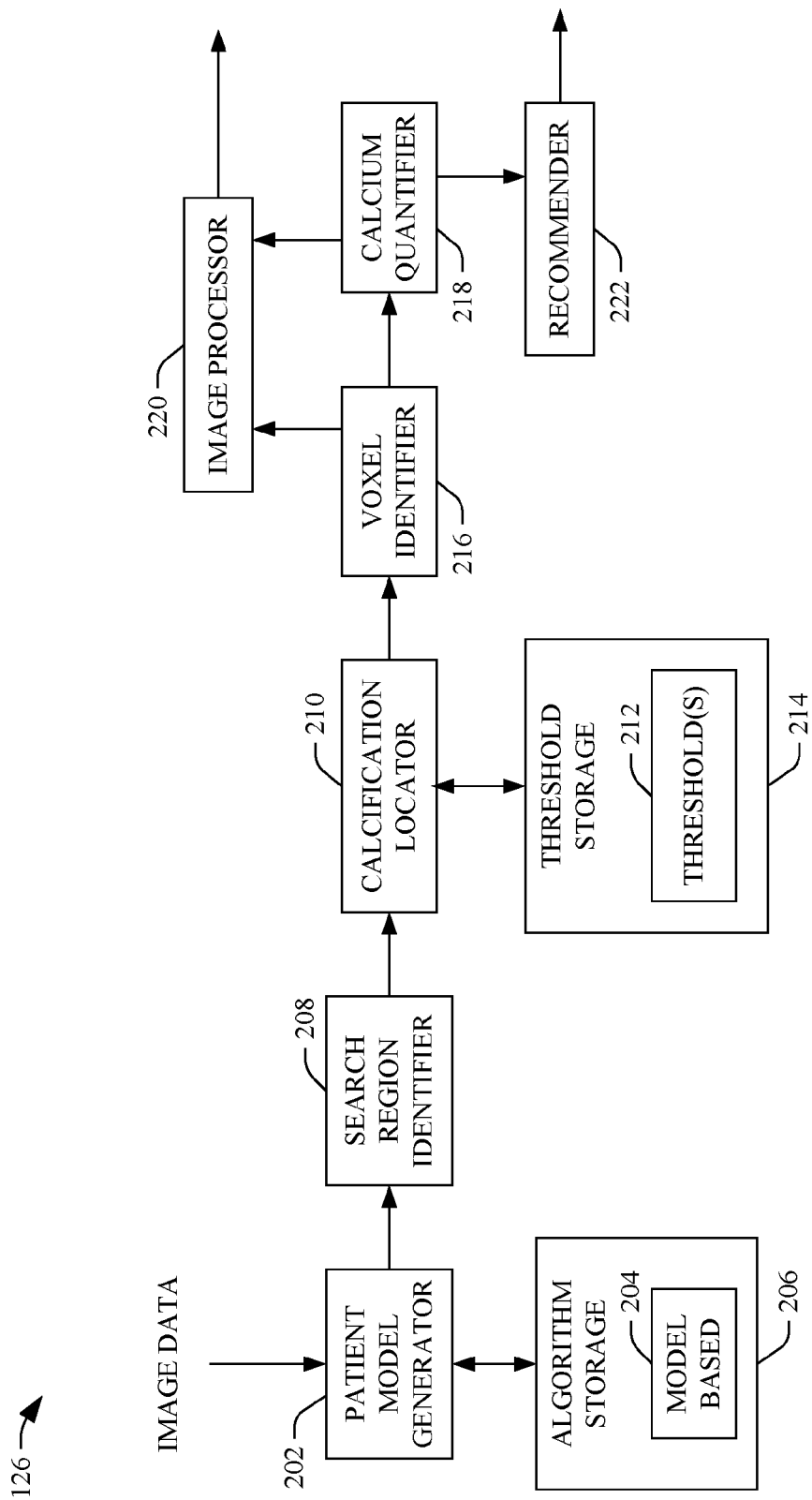
FIG. 2 shows an example of the calcium scorer.

FIG. 2 illustrates an example of the calcium scorer 126.

In this example, the calcium scorer 126 utilizes a model-based segmentation to determine one or more search regions for each part of anatomy of interest throughout a three dimensional (3D) volume of image data and calcium scores are determined for the search regions.

The illustrated calcium scorer 126 includes a patient model generator 202 that generates a (whole body or organ specific) patient specific model based on image data generated by the reconstructor 114 or other system and one or more algorithms. In the illustrated embodiment, the patient model generator 202 employs a model-based algorithm 204 such as a model-based segmentation algorithm to generate the patient model. In the illustrated embodiment, the algorithm 204 and/or one or more other algorithms are stored in algorithm storage 206.

In this example, a patient specific model is generated by adapting a generic cardiovascular system model to images of the specific patient. Generally, the generic model describes the shape, variability and appearance for the individual sub-regions of the cardiovascular system. The patient model generator 202 separates knowledge about the shape from knowledge about image appearance, which facilitates adaptation. In addition, the generic model includes information that controls the sequence and parameters for the model adaptation.

An example of a suitable algorithm is described in O. Ecabert et al., "Automatic Model-Based Segmentation of the Heart in CT images," IEEE Transactions on Medical Imaging, Vol. 27(9), p. 1189-1201, 2008. Another example of a suitable algorithm is described in J. Weese et al., "Patient-Specific Heart Models for Diagnosis and Interventions," MEDICAMUNDI, Vol. 53(3), p. 72-78, 2009. Other algorithms, including other segmentation based and/or non-segmentation based algorithms, are also contemplated herein.

A search region identifier 208 identifies, for structures represented in the image data for which calcifications might be found, one or more search regions based on the patient model. In one non-limiting embodiment, this can be achieved using a region growing approach, starting from the surface of the model, in a region around a landmark, or there could be additional structures in the model which are moving passively with the model during segmentation. Each search region can be uniquely identified or labeled (e.g., via color, text, highlight, etc.) and corresponds to a different region of interest of the cardiovascular system.

By way of non-limiting example, a first search region corresponding to the antrioventricular (AV) leaflet 1 assigned a first color, a second search region corresponding to the AV leaflet 2 assigned a second color, a third search region corresponding to the AV leaflet 3 assigned a third color, a fourth search region corresponding to the mitral assigned a fourth color, a fifth search region corresponding to left ventricalur (LV) outflow assigned a fifth color, a sixth search region corresponding to bulbus assigned a sixth color, a seventh search region corresponding to aorta assigned a seventh color, a eighth search region corresponding to left ostium assigned a eighth color, a ninth search region corresponding to right ostium assigned a ninth color, etc.

A calcification locator 210 locates calcifications in the identified search regions. In one non-limiting embodiment, this can be achieved based on one or more predetermine thresholds 212, such as a threshold from threshold storage 214 and/or other storage. The selected threshold should be as low as possible to identify a calcification, but high enough to distinguish between a calcification and surrounding tissue. The threshold can be computed separately for each part based on the mean intensity and standard deviation in its neighboring structures utilizing the patient mode and/or otherwise.

In one instance, the threshold depends on the image intensities (e.g., an average intensity plus a margin) of the blood pool near to the identified search regions, which depends on the concentration of contrast agent. The identified calcifications can be labeled according to the label of the corresponding search region. For example, if two calcifications are located in the first region and one calcification is located in the second region, then the two calcifications in the first region are similarly labeled with the first color and the calcification in the second region is labeled with the second color.

A voxel identifier 216 identifies one or more groups of voxels in the image data corresponding to the located calcification regions. In one non-limiting embodiment, this may include growing a calcification region outside of an identified search region and identifying voxels in the region outside of the identified search region. Likewise, the identified voxels can be labeled according to the label of the corresponding search region. For example, if first and second regions of voxels are identified for the two located calcifications, the identified voxels are likewise labeled with the first color.

A calcium quantifier 218 quantifies the calcifications in the identified voxels, generating calcium scores for the different search regions and/or structure represented thereby. Any known and/or other calcium scoring algorithm can be utilized to generate the calcium scores.

An image processor 220 variously processes the identified voxels and/or the calcium scores for visual presentation, for example, via the display 132 (FIG. 1) and/or other display.

In one instance, the image processor 220 generates a table for each of the structures corresponding to the identified search regions. By way of example, Table 1 below shows a non-limiting example for the regions listed above. Although not shown, the data in either or both of the columns can be presented in the color corresponding to the above-noted label for the structure.

TABLE 1

Calcium Scores.

| STRUCTURE | CALCIUM SCORE |
|---|---|
| AV Leaflet 1 | 39 mm$^2$ |
| AV Leaflet 2 | 17 mm$^2$ |
| AV Leaflet 3 | 34 mm$^2$ |
| Mitral Valve | 1253 mm$^2$ |
| LV Outflow | 42 mm$^2$ |
| Bulbus | 85 mm$^2$ |
| Aorta | 1579 mm$^2$ |
| Left Ostium | 220 mm$^2$ |
| Right Ostium | 0 mm$^2$ |

Additionally or alternatively, the image processor 220 can map the calcium scores to an anatomical model and visually present the anatomical model and calcium scores in the GUI. The calcium scores can be visually presented with the anatomical model via the colors corresponding to the different structure and/or table entries, alphanumeric text, highlighting, and/or otherwise.

Additionally or alternatively, the image processor 220 can map the calcium scores to an anatomical model and visually present only the anatomical model in the GUI. In this instance, the user can hover a mouse pointer or other pointing device over a region of interest in the GUI representing the anatomy of interest, click on such a region with a mouse or the like, select the region of interest via a keyboard, and/or otherwise identify the region of interest. In response, the calcium score can be displayed as discussed herein via alphanumeric character, color, audio, and/or otherwise.

Additionally or alternatively, the image processor 220 can map the calcium scores to the image data such as transverse (axial), coronal, sagittal, and/or oblique slices of the volumetric image data, 3D or 4D renderings, and/or otherwise visually displayed image data. In this instance, the calcium scores can be presented as discussed herein in which the image data is connected to the information in Table 1 and/or presented upon identifying a region of interest.

Additionally or alternatively, the image processor 220 can map the calcium scores onto the surface of the anatomical model. In this instance, grey value profiles can computed perpendicular to the surface of the model. The values can be normalized such that the local blood pool image intensity is mapped to zero. Then, the integral along the profile is computed and mapped to the surface of the patient profile for visualization.

Color or other indicia can be used to indicate a relative or absolute degree, severity, risk, etc. (e.g., red for high severity and green for low severity, one or more other colors for severity in between). A transparency setting can be used to see through the top surface of the anatomical model to underlying surface(s) with the indicia which otherwise is hidden by the top surface and not visible. If no quantitative measure is mapped to the surface, the maximum intensity along the profile can be used without normalization.

Various known visualization techniques, including zoom, pan, rotate, transparency, segmentation (removal of structure), etc. can be utilized with the visually presented data.

A recommender 222 generates a signal indicative of a recommended action (and optionally other information) based on the one or more of the calcium scores determined by the calcium quantifier 218. In one instance, the recommender 222 generates a recommendation for particular anatomical structure identified and assigned a calcium score based on the assigned calcium score. In another instance, the recommender 222 generates the recommendation for the particular anatomical structure based on a calcium score assigned to other structure. In yet another instance, the recommender 222 generates the recommendation for the particular anatomical structure based on a compilation of calcium scores for multiple structures assigned calcium scores.

Suitable recommendations include, but are not limited to, one or more interventional procedures, one or more further tests, a dietary change for the patient, a activity change for the patient, a medication for the patient, and/or other recommendation. By way of example, a recommendation may include recommending an access point for a device to the implanted such as minimally invasive aortic valve implantation. In another example, a recommendation may include recommending a size of a device to be implanted such as a diameter of a stent to be implanted, and provide information such as likely stent stability. The above examples are not limiting, and other recommendations and/or information may be provided by the recommender 222.

Figure 3:
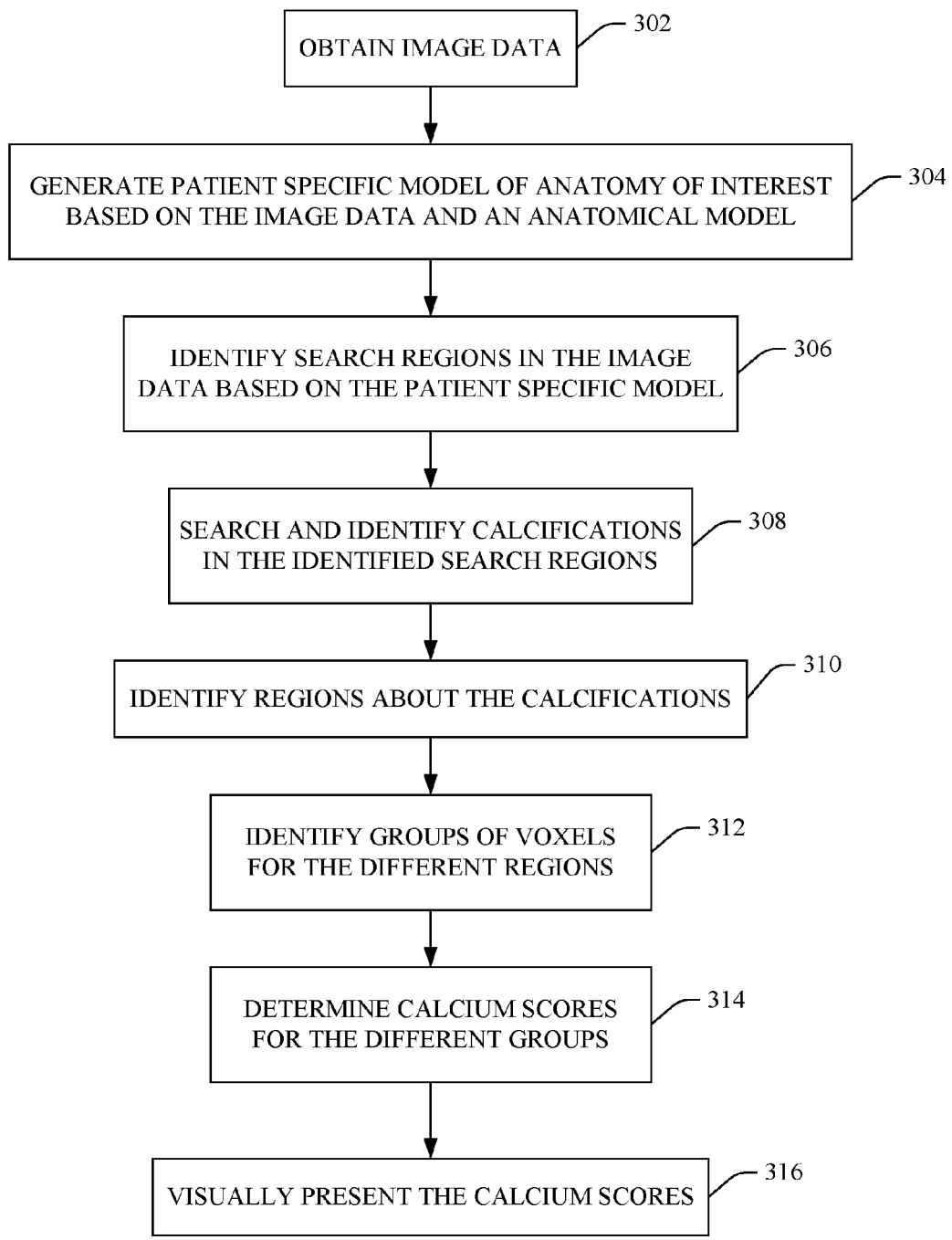
FIG. 3 illustrates a method for facilitating calcium scoring.

FIG. 3 illustrates an example method for facilitating determining calcium scores for one or more sub-regions of interest of the cardiovascular system.

It is to be appreciated that the ordering of the above acts is not limiting. As such, other orderings are contemplated herein. In addition, one or more acts may be omitted and/or one or more additional acts may be included.

At 302, image data is obtained. The image data can be generated by the reconstructor 114 and/or other system.

At 304, a patient specific model of anatomy of interest is generated based on the image data and a generic anatomical model.

At 306, search regions are identified in the image data based on the patient model.

At 308, calcifications are identified in one or more of the search regions. As described herein, thresholding and/or other techniques can be employed.

At 310, regions about the identified calcifications are determined.

At 312, groups of voxels corresponding to the different regions are identified.

At 314, calcium scores are determined respectively for the different groups.

At 316, the calcium scores are variously visually presented.

As described herein, in one instance this may include generating and presenting a table mapping regions of interest to calcium scores, visually mapping the calcium scores to corresponding locations on an anatomical model via color or otherwise, associating the calcium scores to corresponding locations on an anatomical model where selecting a location results in presentation of the associated calcium score, visually mapping the calcium scores on a surface of the anatomical model to indicate a relative or absolute severity of the calcium deposit.

The above may be implemented by way of computer readable instructions, which when executed by a computer processor(s), cause the processor(s) to carry out the described acts. In such a case, the instructions are stored in a computer readable storage medium associated with or otherwise accessible to the relevant computer. The acts need not be performed concurrently with data acquisition.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

What is claimed is:

1. A method, comprising:
   identifying a plurality of different anatomical sub-regions of a cardiovascular system of a subject in image data of the subject based on a subject specific cardiovascular anatomical model, wherein the plurality of different anatomical sub-regions corresponds to regions where calcifications occur;
   searching for calcifications in the sub-regions based on voxel grey value intensity values of the image data,
   identifying calcifications in a sub-region using a pre-determined threshold, wherein a first threshold is used for a first sub-region of the plurality of different anatomical sub-regions, a second threshold is used for a second sub-region of the plurality of different anatomical sub-regions, and the first and second thresholds are different;
   generating a signal indicative of one or more regions of voxels of the image data respectively corresponding to sub-regions including identified calcifications;
   determining calcium scores for at least one of the sub-regions
   determining relative severities for the calcium scores;
   assigning a different color to the different severities;
   generating a mapping between the relative severities and a surface of the subject specific cardiovascular anatomical model; and
   visually presenting the subject specific cardiovascular anatomical model, using the different colors assigned to the severities to identify the relative severities in corresponding sub-regions.

2. The method of claim 1, further comprising:
   obtaining a generic anatomical model of the cardiovascular system; and
   generating the subject specific cardiovascular anatomical model based on the image data and the generic anatomical model of the cardiovascular system.

3. The method of claim 1, wherein the threshold is based on intensity values of a blood pool near the region.

4. The method of claim 3, wherein the threshold is based on an average value of the intensity values plus a margin.

5. The method of claim 1, wherein the threshold is based on a mean intensity and standard deviation in structures neighboring the sub-region in the subject specific cardiovascular model.

6. The method of claim 1, further comprising:
   growing at least one of the regions of voxels outside of a corresponding search sub-region into an expanded region; and
   determining a calcium score based on the expanded region.

7. The method of claim 1, further comprising:
   visually presenting the calcium scores along with indicia indicating respective sub-regions of the anatomical sub-regions.

8. The method of claim 7, further comprising:
   associating a different color with each of the sub-regions;
   visually presenting the calcium scores along and with the indicia, using the respective colors for the sub-regions; and
   visually presenting the subject specific cardiovascular anatomical model, using the respective colors of the sub-regions to identify the sub-regions in the subject specific cardiovascular anatomical model.

9. The method of claim 1, further comprising:
   generating a mapping between the calcium scores and the subject specific cardiovascular anatomical model;
   visually presenting the subject specific cardiovascular anatomical model; and
   visually presenting a calcium score for a sub-region in response to receiving a signal indicative of a user input selecting the sub-region.

10. The method of claim 1, further comprising:
    assigning a transparency value to the surface; and
    visually presenting the subject specific cardiovascular anatomical model, using the different colors to identify the relative severities in corresponding sub-regions behind the surface.

11. A computing system, comprising:
    a processor that automatically determines a plurality of different groups of voxels of image data of a subject, wherein each group of voxels corresponds to a different sub-region of a cardiovascular system of the subject and each group of voxels corresponds to a region that includes a calcification identified in the image data, wherein the processor determines calcium score values for the plurality of different groups, determines relative severities for the calcium scores, assigns a different color to the different severities, generates a mapping between the relative severities and a surface of a subject specific cardiovascular anatomical model, and visually presents the subject specific cardiovascular anatomical model, using the different colors to identify the relative severities in corresponding sub-regions, wherein the processor is programmed to recommend at least one of an access point for an implant or a size of the implant based on a calcium score for a given sub-region.

12. The system of claim 11, wherein the processor determines the plurality of different sub-regions based on a subject specific cardiovascular anatomical model.

13. The system of claim 12, wherein the processor determines the subject specific cardiovascular anatomical model based on the image data and a generic anatomical model of the cardiovascular system, using a model-based segmentation.

14. The system of claim 11, wherein the processor identifies calcifications based on a pre-determined voxel intensity value threshold.

15. The system of claim 14, wherein the threshold is based on at least one of a blood pool near the sub-region or tissue surrounding the sub-region.

16. The system of claim 11, wherein the processor identifies the sub-regions by growing a region around a landmark starting from a surface of the subject specific cardiovascular model.

17. The system of claim 11, wherein the processor visually presents the calcium scores along with indicia indicating respective sub-regions of the anatomical sub-regions.

18. The system of claim 17, wherein the processor associates a different color with each of the sub-regions, visually presents the calcium scores along and with the indicia, using the respective colors of the sub-regions, and visually presents the subject specific cardiovascular anatomical model, using the respective colors of the sub-regions to identify the sub-regions in the subject specific cardiovascular anatomical model.

19. The system of claim 17, wherein the processor generates a mapping between the calcium scores and the subject specific cardiovascular anatomical model, visually presents the subject specific cardiovascular anatomical model, and visually presents a calcium score for a sub-region in response to receiving a signal indicative of a user selected sub-region.

20. The system of claim 11, wherein the processor is programmed to recommend a course of action based on a calcium score for a given sub-region.

21. The system of claim 11, wherein the processor is programmed to recommend a course of action based on a compilation of calcium scores for multiple sub-regions.

22. A non-transitory computer readable medium encoded with computer executable instructions, which, when executed by a computer processor, causes the computer processor to:

identify a plurality of different anatomical sub-regions of a cardiovascular system of a subject in image data of the subject based on a subject specific cardiovascular anatomical model, wherein the plurality of different regions corresponds to regions where calcifications occur;

search for and identify calcifications in the sub-regions based on voxel grey value intensity values of the image data;

generate a signal indicative of one or more regions of voxels of the image data respectively corresponding to sub-regions including identified calcifications;

determine calcium scores for at least one of the sub-regions determine relative seventies for the calcium scores;

assign a different color to the different seventies;

generate a mapping between the relative seventies and a surface of the subject specific cardiovascular anatomical model;

assign a transparency value to the surface; and visually present the subject specific cardiovascular anatomical model, using the different colors assigned to the seventies to identify the relative seventies in corresponding sub-regions behind the surface.

* * * * *